United States Patent
Amanatullah

(10) Patent No.: US 12,343,259 B2
(45) Date of Patent: *Jul. 1, 2025

(54) EXPANDABLE AUGMENT SYSTEM FOR ACETABULAR CUP

(71) Applicant: Arthrology Consulting, LLC, Menlo Park, CA (US)

(72) Inventor: Derek Amanatullah, Menlo Park, CA (US)

(73) Assignee: Arthrology Consulting, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,344

(22) Filed: Feb. 28, 2024

(65) Prior Publication Data

US 2024/0197480 A1 Jun. 20, 2024

Related U.S. Application Data

(63) Continuation of application No. 17/455,893, filed on Nov. 19, 2021, now Pat. No. 11,944,544.

(51) Int. Cl.
*A61F 2/30* (2006.01)
*A61F 2/34* (2006.01)

(52) U.S. Cl.
CPC .......... *A61F 2/30734* (2013.01); *A61F 2/34* (2013.01); *A61F 2002/30471* (2013.01); *A61F 2002/3054* (2013.01); *A61F 2002/30579* (2013.01); *A61F 2002/30736* (2013.01)

(58) Field of Classification Search
CPC ............................................ A61F 2002/30736
See application file for complete search history.

(56) References Cited

U.S. PATENT DOCUMENTS

| | | | |
|---|---|---|---|
| 5,176,711 | A | 1/1993 | Grimes |
| 5,192,329 | A | 3/1993 | Christie et al. |
| 5,290,315 | A | 3/1994 | DeCarlo, Jr. |
| 5,370,704 | A | 12/1994 | DeCarlo, Jr. |
| 5,928,288 | A | 7/1999 | Wilson |
| 6,187,050 | B1 | 2/2001 | Khalili et al. |
| 7,942,880 | B2 | 5/2011 | Bertram, III |
| 7,985,260 | B2 | 7/2011 | Keefer et al. |
| 7,993,408 | B2 | 8/2011 | Meridew et al. |
| 8,535,385 | B2 | 9/2013 | Hanssen et al. |
| 8,728,168 | B2 | 5/2014 | Hanssen et al. |
| 8,828,009 | B2 | 9/2014 | Allen et al. |
| 8,900,320 | B2 | 12/2014 | Frederick et al. |
| 9,468,530 | B2 | 10/2016 | Quinn et al. |

(Continued)

*Primary Examiner* — Melanie R Tyson
*Assistant Examiner* — Yasniary De La Caridad Morales
(74) *Attorney, Agent, or Firm* — Knobbe, Martens, Olson & Bear, LLP

(57) ABSTRACT

An expandable augment system is provided for use with an acetabular cup. The expandable augment system can include an expandable augment module that is adjustable in size and that can be adjusted incrementally between a fully collapsed state and an expanded state. A first portion of the expandable augment module is attachable to an outer surface of an acetabular cup and a second portion of the expandable augment module is attachable to bone or to a fixed augment module (e.g., a fixed angle augment module) that is attached to bone and interposed between the adjustable augment module and bone.

17 Claims, 12 Drawing Sheets

(56) References Cited

U.S. PATENT DOCUMENTS

| | | |
|---|---|---|
| 9,504,577 B2 | 11/2016 | Frederick et al. |
| 9,539,096 B2 | 10/2017 | Hanssen et al. |
| 9,901,451 B2 | 2/2018 | Conway et al. |
| 9,949,836 B2 | 4/2018 | Quinn et al. |
| 10,092,404 B2 | 10/2018 | Hanssen et al. |
| 10,098,743 B2 | 10/2018 | Hanssen et al. |
| 10,159,572 B2 | 12/2018 | Bailey et al. |
| 10,201,426 B2 | 2/2019 | Hanssen et al. |
| 10,265,177 B2 | 4/2019 | Quinn et al. |
| 10,350,073 B2 | 7/2019 | Anderson et al. |
| 10,646,346 B2 | 5/2020 | Hanssen et al. |
| 10,653,526 B2 | 5/2020 | Hanssen et al. |
| 10,687,947 B2 | 6/2020 | Berend |
| 10,751,186 B2 | 8/2020 | Macke |
| 10,806,587 B2 | 10/2020 | Hanssen |
| 10,806,588 B2 | 10/2020 | Bailey |
| 11,241,318 B2 | 2/2022 | Biedermann |
| 11,944,544 B2 | 4/2024 | Amanatullah |
| 2003/0065397 A1 | 4/2003 | Hanssen et al. |
| 2008/0021568 A1 | 1/2008 | Tulkis et al. |
| 2011/0288650 A1* | 11/2011 | Ries .................. A61F 2/34 623/22.32 |
| 2012/0016485 A1 | 1/2012 | Sharp |
| 2012/0083895 A1 | 4/2012 | Conway et al. |
| 2012/0089235 A1 | 4/2012 | Conway et al. |
| 2012/0209384 A1 | 8/2012 | Arnold et al. |
| 2015/0057756 A1 | 2/2015 | Lang et al. |
| 2015/0094813 A1 | 4/2015 | Lechmann et al. |
| 2015/0100128 A1 | 4/2015 | Glerum et al. |
| 2015/0257894 A1 | 9/2015 | Levy et al. |
| 2015/0289988 A1 | 10/2015 | Ashley et al. |
| 2016/0317307 A1 | 11/2016 | Bailey et al. |
| 2017/0231778 A1* | 8/2017 | Overes ............. A61F 2/4425 623/17.16 |
| 2017/0231781 A1 | 8/2017 | Kraemer |
| 2018/0325673 A1 | 11/2018 | Berend et al. |
| 2019/0282366 A1 | 9/2019 | Anderson et al. |
| 2020/0345499 A1 | 11/2020 | Macke |

\* cited by examiner

EXPANDABLE AUGMENT SYSTEM FOR ACETABULAR CUP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure is directed to an augment system for an acetabular cup for use in hip joint replacement surgical procedures, and more particularly to an expandable and modular augment system for an acetabular cup.

Description of the Related Art

Hip joint replacement surgical procedures involve the implantation of an acetabular cup in the pelvis bone that receives a liner and a head of a femoral stem implant that is inserted into the femur bone. Where the pelvis has defects and/or loss of bone, an augment is needed to secure the acetabular cup in place.

SUMMARY

In accordance with one aspect of the disclosure, an expandable augment system is provided for use with an acetabular cup. The expandable augment system can include an expandable augment module that is adjustable in size that can be adjusted incrementally between a fully collapsed state and an expanded state. A first portion of the expandable augment module is attachable to an outer surface of an acetabular cup and a second portion of the expandable augment module is attachable to bone or to a fixed augment module (e.g., a fixed angle augment module) that is attached to bone and interposed between the adjustable augment module and bone. Advantageously, the expandable augment can be used to account for different amounts or shape of bone loss or defects in the pelvis with the same augment module, reducing the number of augments needed for a surgical procedure where loss of bone or defects are present. Additionally, the expandable augment can advantageously be adjusted in size incrementally, allowing for its use with different sized acetabular cups.

In accordance with an aspect of the disclosure, an augment for an acetabular cup is provided. The augment includes and expandable augment body. The expandable augment body comprises a first plate configured to couple with a bone or a fixed augment module, the first plate having one or more first openings configured to receive therethrough corresponding one or more first fasteners. The expandable augment body also comprises a second plate configured to couple to an outer surface of an acetabular cup, the second plate connected to the first plate and configured to pivot relative to the first plate between a first position where the second plate is proximate the first plate along its length and a second position where at least a portion of the second plate is spaced from the first plate. The second plate has one or more second openings configured to be coaxial with the one or more first openings when in the first position, the one or more second openings having a larger size than the one or more first openings.

In accordance with another aspect of the disclosure, an augment kit for an acetabular cup is provided. The kit comprises an expandable augment body. The expandable augment body comprises a first plate having one or more first openings configured to receive therethrough corresponding one or more first fasteners. The expandable augment body also comprises a second plate configured to couple to an outer surface of an acetabular cup, the second plate connected to the first plate and configured to pivot relative to the first plate between a first position where the second plate is proximate the first plate along its length and a second position where at least a portion of the second plate is spaced from the first plate. The second plate has one or more second openings configured to be coaxial with the one or more first openings when in the first position, the one or more second openings having a larger size than the one or more first openings. The kit also comprises one or more fixed augment modules. Each of the fixed augment modules has a third plate and a fourth plate connected to the third plate and extending at a fixed angle relative to the third plate. The third plate has one or more openings configured to receive corresponding fasteners therethrough to couple the fixed augment module to bone. The fourth plate has one or more openings configured to receive the one or more first fasteners therethrough to couple the fixed augment module to the expandable augment body. At least one of the one or more fixed augment modules has a different fixed angle.

In accordance with another aspect of the disclosure, a method for implanting an acetabular cup is provided. The method comprises evaluating a size of an acetabular hole and one or more defects in a pelvis bone proximate the acetabulum. The method also comprises attaching an expandable augment module to the pelvis bone or to a fixed angle augment module attached to the pelvis bone. The method also comprises adjusting a size of the expandable augment module to contact an acetabular cup. The method also comprises applying cement between the acetabular cup and bone, and applying cement between plates of the expandable augment module or plates of the fixed angled augment module to thereby fix the acetabular cup in the bone.

DETAILED DESCRIPTION

Disclosed herein are augment modules for use in a hip joint surgical procedure, such as hip joint revision surgery, where an acetabular cup is implanted in the acetabulum of the pelvis bone. The acetabular cup can at least partially receive a liner, which can at least partially receive a ball of a femoral stem implant. The augment modules disclosed below advantageously provide structural support to the acetabular cup where bone loss or defects in the pelvis bone prevent the implantation of the acetabular cup on its own (e.g., without the use of an augment).

Figure 1:
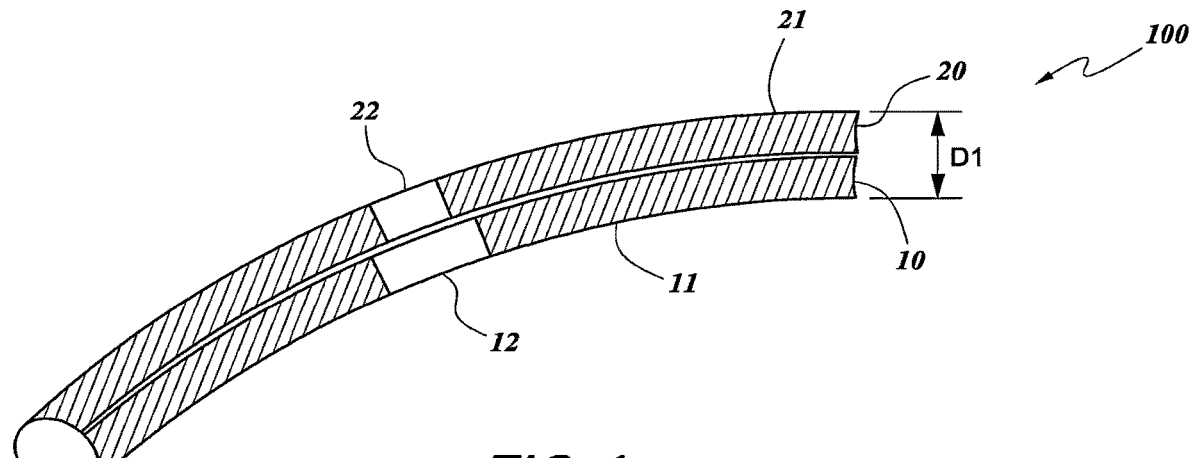
FIG. 1 is a schematic cross-sectional view of an expandable augment for use with an acetabular cup, the expandable augment in a first position.
Figure 2:
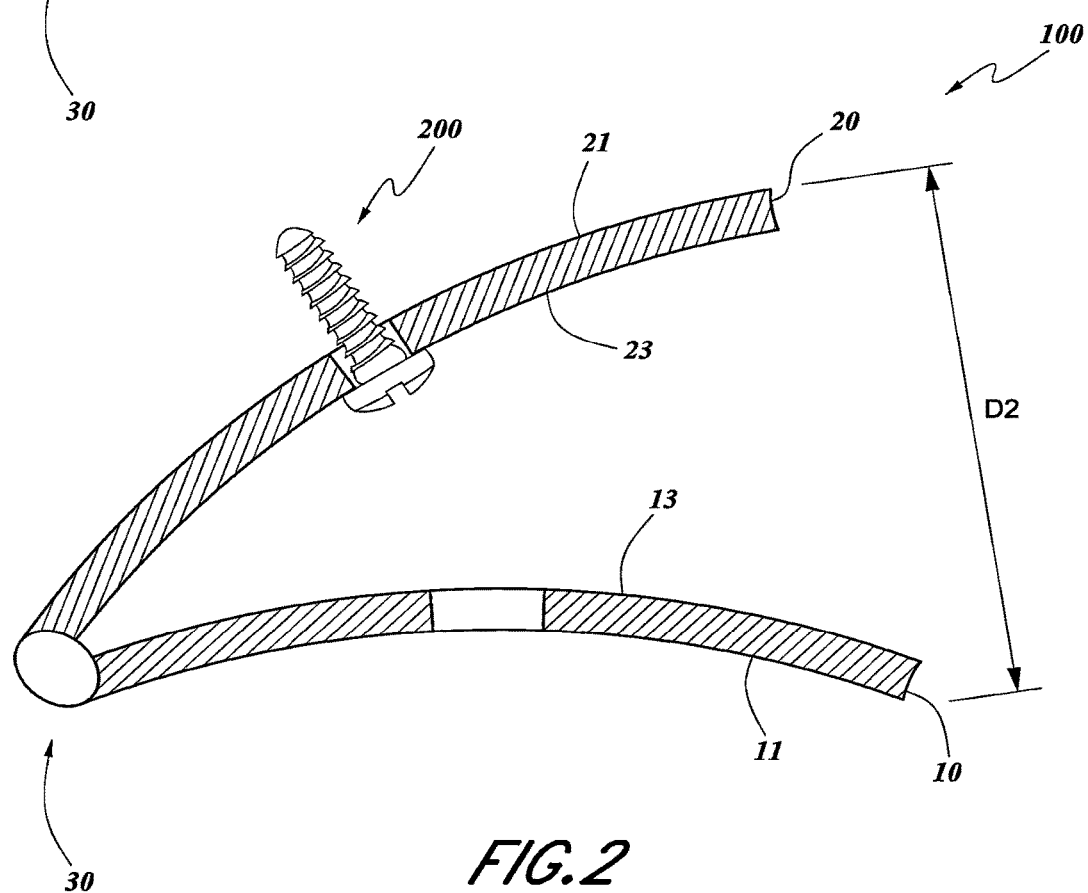
FIG. 2 is a schematic cross-sectional view of the expandable augment of FIG. 1, the expandable augment in a second position.
Figure 3:
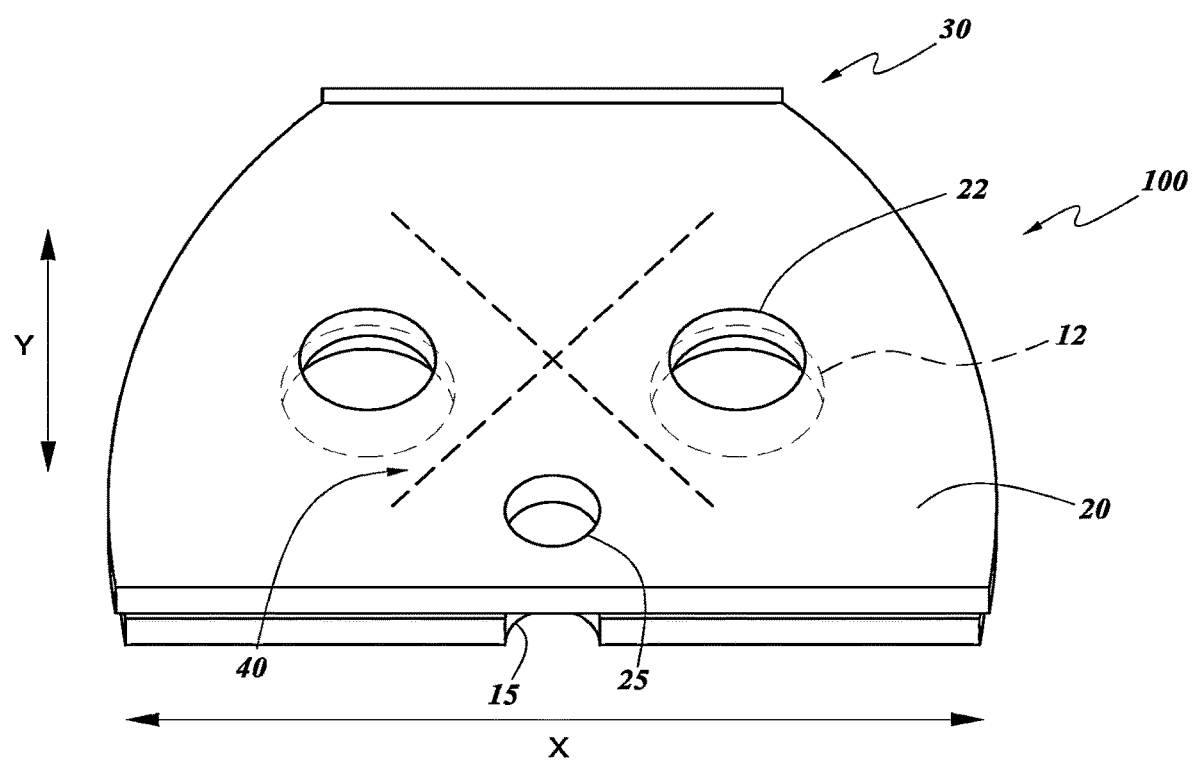
FIG. 3 is a schematic top view of the expandable augment of FIG. 1.

FIGS. 1-4 show an expandable augment module 100 with a first plate 10 and a second plate 20 movably coupled to the first plate 10 by a hinge 30. In one implementation, the first and second plates 10, 20 can have the same thickness. In another implementation, the first and second plates 10, 20 can have different thicknesses. In one implementation, the first and second plates 10, 20 can span approximately the same area. In another implementation the first and second plates 10, 20 can have different areas (e.g., have different shapes). The first and second plates 10, 10 can be curved (e.g., in an X direction and a Y direction, as shown in FIG. 3). Advantageously, the first plate 10 can be curved so that it has a contour that approximates a contour of an outer surface of an acetabular cup AC (see FIG. 8). In one implementation, the first plate 10 and second plate 20 have approximately the same curvature. In another implementation, the first plate 10 and second plate 20 can have different curvatures (e.g., the second plate 20 can have a larger radius of curvature than the first plate 10). In one implementation, the expandable augment module 100 can be made of metal (e.g., titanium). In another implementation, the expandable augment module 100 can be made of a biocompatible polymer material (e.g., polyethylene, cross-linked polyethylene).

The outer surface 11 of the first plate 10 and the outer surface 21 of the second plate 20 can be porous to facilitate attachment to bone cement and/or bone to aid in solidifying the implantation of the expandable augment module 100. For example, where the expandable augment module 100 is attached to bone and to an acetabular cup (e.g., as shown in FIG. 8), the porous outer surface 21 of the second plate 20 can facilitate bone in or on growth to aid in solidifying the implantation of the expandable augment module 100 to bone. The inner surface 13 of the first plate 10 and the inner surface 23 of the second plate 20 can be porous or rough (e.g., not smooth) to facilitate attachment of bone cement thereto.

FIG. 1 shows the expandable augment module 100 in a first position (e.g., a closed, collapsed or retracted position) where the first plate 10 is adjacent (e.g., in contact with) the second plate 20. In the first position, the expandable augment module 100 can provide a first spacing or thickness D1 (e.g., maximum distance between an outer surface of the first plate 10 and an outer surface of the second plate 20). In one example, the first spacing or thickness D1 can be approximately 5 mm. However, the first pacing or thickness D1 can have other suitable dimensions. FIG. 2 shows the expandable augment module 100 in a second position (e.g., an open or expanded position) where at least a portion of the first plate 10 is spaced (e.g., separated by a space or opening) from the second plate 20. In the second position, the expandable augment module 100 can provide a second spacing or thickness D2 (e.g., maximum distance between an outer surface of the first plate 10 and an outer surface of the second plate 20). In one example, the first spacing or thickness D1 can be approximately 30 mm. However, the second spacing or thickness D2 can have other suitable dimensions. Though FIG. 2 shows one expanded position for the expandable augment module 100, one of skill in the art will recognize that multiple (e.g. a plurality of) expanded positions (e.g., at 5 mm, 10 mm, 15 mm, 20 mm, 25 mm, 30 mm) between the first position (shown in FIG. 1) and a maximum expanded position are possible, to vary a spacing or thickness D provided by the expandable augment module 100. In one implementation, the expandable augment system 100 can be incrementally expanded (e.g., in 5 mm increments) between the first position (e.g., closed, collapsed or retracted position in FIG. 1) and a maximum expanded position (e.g., to multiple intermediate expanded positions). In another implementation, the expandable augment system 100 can be continuously adjustable between the first position and a maximum expanded position.

Figure 4:
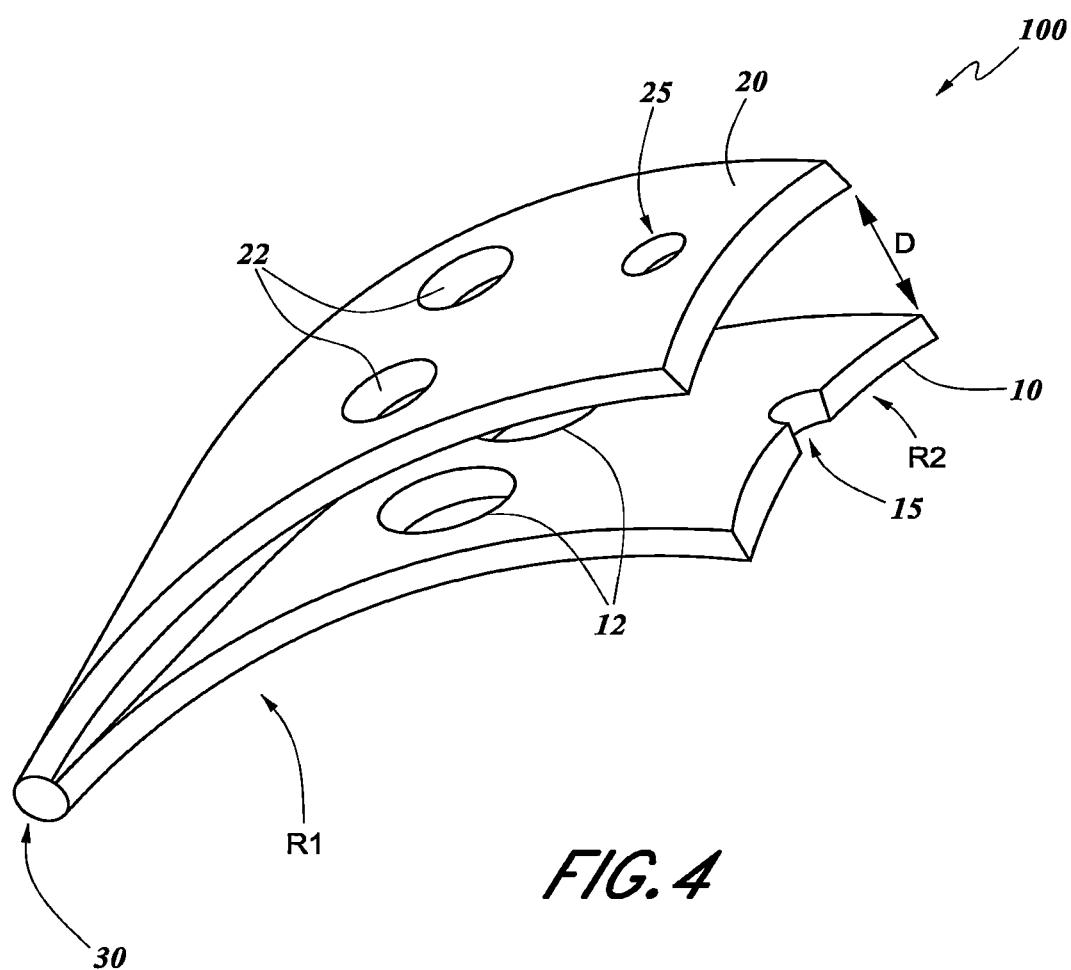
FIG. 4 is a schematic perspective view of the expandable augment of FIG. 3.

The first plate 10 has one or more openings (e.g., first openings) 12 that extend through (e.g., completely through) the first plate 10. The second plate has one or more openings (e.g., second openings) 22 that extend through (e.g., completely through) the second plate 20. The openings 12 and 22 are aligned (e.g., coaxial) when the expandable augment module 100 is in the first position (e.g., closed, collapsed or retracted position shown in FIG. 1). The openings 12 are larger than the openings 22 and allow one or more fasteners 200 to be inserted through the openings 12 and openings 22 while the expandable augment module 100 is in the first position (shown in FIG. 1), such as to fix or attach the expandable augment module 100 to bone (e.g., the pelvis bone), and advantageously allows the adjustment of the first plate 10 away from the second plate 20 (e.g., to move the expandable augment module 100 to the second position, shown in FIG. 2) while the second plate 20 is fixed (by the fastener(s) 200) to bone. For example, the openings 22 can be larger in size than a head of the fastener(s) 200, whereas the openings 12 can be smaller in size than the head of the fastener(s) 200. As shown in FIG. 4, the expandable augment module 100 can have one or more openings 25 in the second plate 20 that align with one or more cutout 15 in a rim of the first plate 10. The opening(s) 25 and cutout(s) 15 can be sized to receive a wire to provisionally secure the expandable augment module 100 to bone (e.g., by inserting the wire through the cutout(s) 15 and the opening(s) or hole(s) 25 and into bone) prior to securing the expandable augment module 100 with the fastener(s) 200. Advantageously, the cutout(s) 15 allow the wire to be removed (e.g., escape) by moving the wire laterally relative to the cutout(s) 15.

Figure 5:
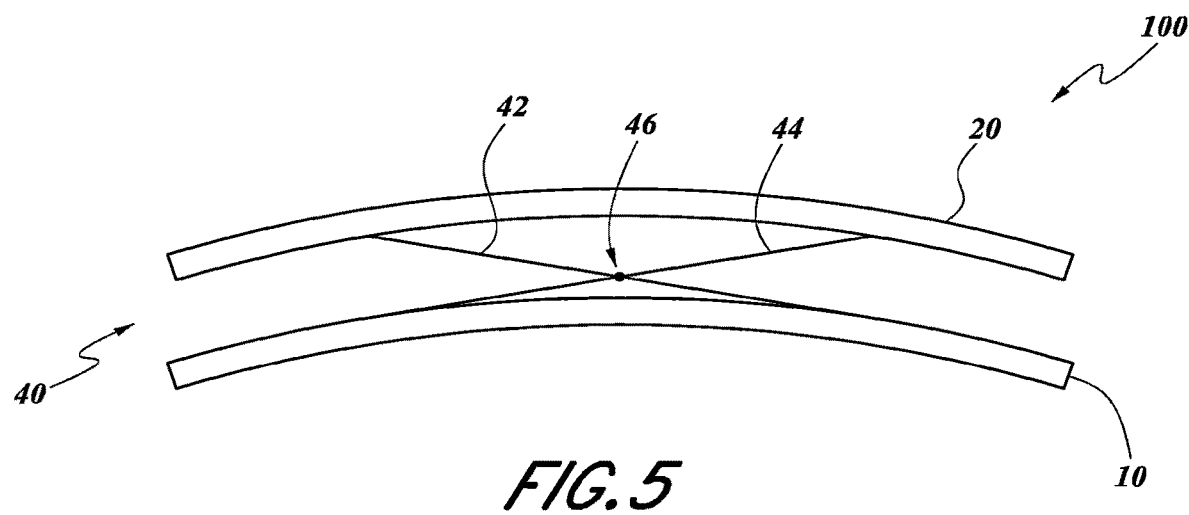
FIG. 5 is a schematic view of an expandable augment with a support structure, in a first position.
Figure 6:
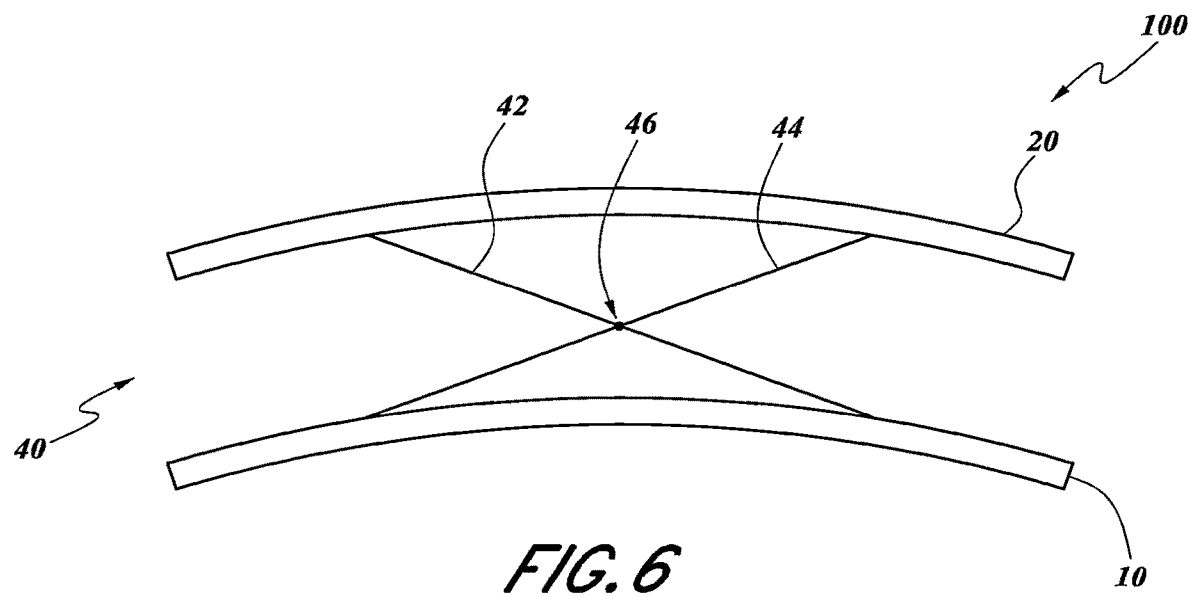
FIG. 6 is a schematic view of an expandable augment with a support structure, in a second position.

FIGS. 5-6 show an implementation of the expandable augment system 100 that (optionally) includes a support structure 40 having a first support member 42 and a second support member 44 that extend between the first plate 10 and the second plate 20. The first and second support members 42, 44 are movably coupled to each other via a pivot or joint 46 and can be movably coupled (e.g., slidably coupled) to the first and second plates 10, 20, advantageously allowing the first and second support members 42, 44 to move between a first position (shown in FIG. 5), where at least a portion of the first and second plates 10, 20 are relatively closer to each other, and second position (shown in FIG. 6), where at least a portion of the first and second plates 10, 20 are relatively farther apart from each other. The first and second support members 42, 44 advantageously provide structural support to the expandable augment module 100 when in an expanded position (e.g., in a position other than the first position shown in FIG. 1) to facilitate maintaining the expandable augment module 100 in the expanded position. In one implementation, the support structure can include a ratchet-like assembly that allows the first plate 10 to move relative to the second plate 20 incrementally, the ratchet system allowing the expandable augment module 100 to retain its expanded position at each increment of its expansion.

Figure 7A:
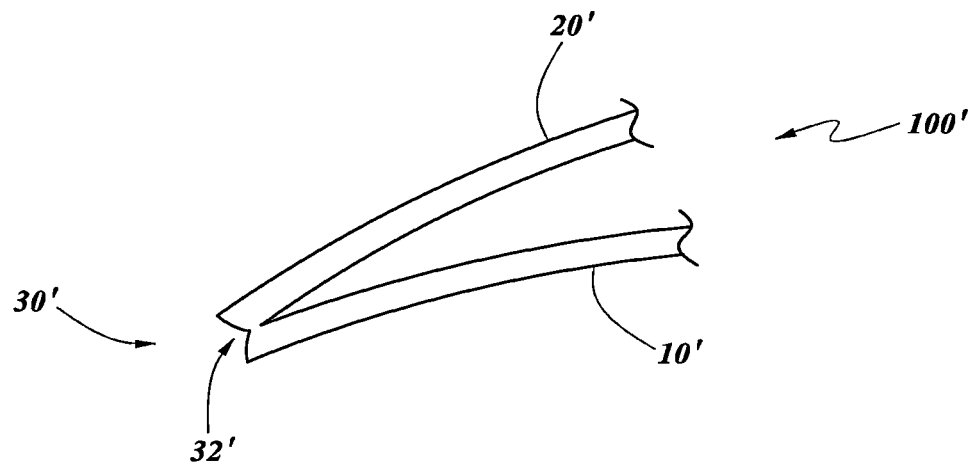
FIG. 7A is a schematic partial view of a hinge portion of the expandable augment.

FIG. 7A shows a portion of an expandable augment module 100'. Some of the features of the expandable augment module 100' are similar to features of the expandable augment module 100 in FIGS. 1-4. Thus, reference numerals used to designate the various components of the expandable augment module 100' are identical to those used for identifying the corresponding components of the expandable augment module 100 in FIGS. 1-4, except that a "'" has been added to the numerical identifier. Therefore, the structure and description for the various features of the expandable augment module 100 in FIGS. 1-4 are understood to also apply to the corresponding features of the expandable augment module 100' in FIG. 7A, except as described below.

The expandable augment module 100' differs from the expandable augment module 100 in that the hinge 30' is a living hinge. The material of the first plate 10' is one piece with the material of the second plate 20' but has a portion 32' with reduced thickness 32' at the hinge 30' that facilitates the movement of the first plate 10' relative to the second plate 20' about the hinge 30'.

Figure 7B:
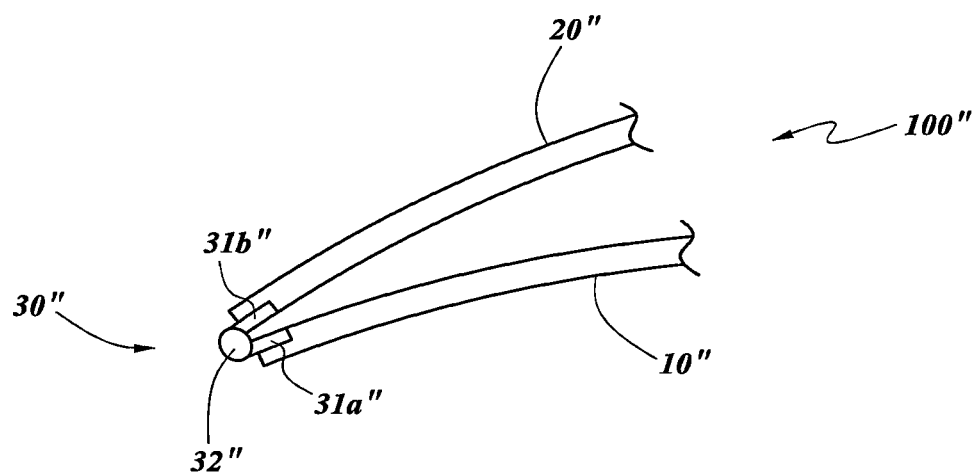
FIG. 7B is a schematic partial view of a hinge portion of the expandable augment

FIG. 7B shows a portion of an expandable augment module 100". Some of the features of the expandable augment module 100" are similar to features of the expandable augment module 100 in FIGS. 1-4. Thus, reference numerals used to designate the various components of the expandable augment module 100" are identical to those used for identifying the corresponding components of the expandable augment module 100 in FIGS. 1-4, except that a "''" has been added to the numerical identifier. Therefore, the structure and description for the various features of the expandable augment module 100 in FIGS. 1-4 are understood to also apply to the corresponding features of the expandable augment module 100" in FIG. 7B, except as described below.

The expandable augment module 100" differs from the expandable augment module 100 in that the hinge 30" is a separate component from the first plate 10" and second plate 20". The hinge 30" has a first member 31a" attached to the first plate 10" and a second member 31b" attached to the second member 31b". The first and second members 31a", 31b" are pivotally coupled to each other by a pin 32". The hinge 30" facilitates the movement of the first plate 10" relative to the second plate 20" about the pin 32".

Figure 8A:
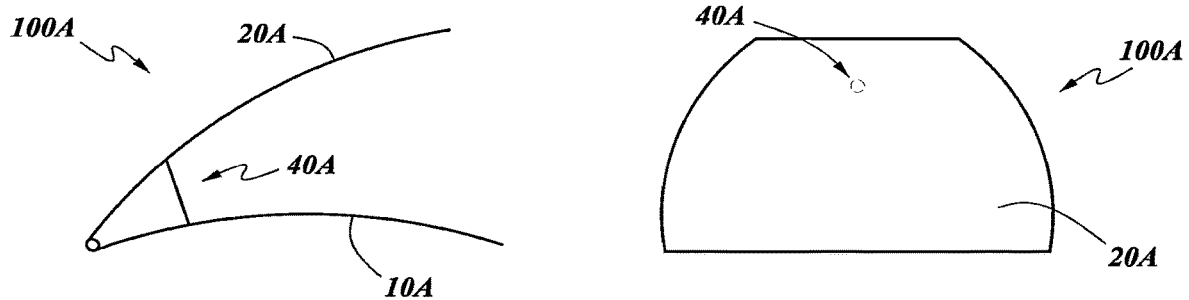
FIG. 8A shows a schematic side view and top view of an expandable augment with a support structure.

FIG. 8A shows a schematic side view (left image) and top view (right image) of an expandable augment module 100A. Some of the features of the expandable augment module 100A are similar to features of the expandable augment module 100, 100', 100" in FIGS. 1-7B. Thus, reference numerals used to designate the various components of the expandable augment module 100A are identical to those used for identifying the corresponding components of the expandable augment module 100, 100', 100" in FIGS. 1-7B, except that an "A" has been added to the numerical identifier. Therefore, the structure and description for the various features of the expandable augment module 100, 100', 100" in FIGS. 1-7B are understood to also apply to the corresponding features of the expandable augment module 100A in FIG. 8A, except as described below.

The expandable augment module 100A differs from the expandable augment module 100 in that the support structure 40A is a post (e.g., linear member) 40A that extends between the first plate 10A and the second plate 20A. The post 40A can be a separate component inserted between the first plate 10A and the second plate 20A. In another implementation, the post 40A can be integral with the first plate 10A and the second plate 20A. the post 40A can be disposed toward a rear of the expandable augment 100A (e.g., close to the location of the hinge). In one implementation, the post 40A is expandable (e.g., has one portion that telescopes relative to a second portion to allow the length of the post 40A to change), such as incrementally between different length setpoints, which can advantageously support the expandable augment 100A in different expanded positions (e.g., between 5 mm and 30 mm at the opening of the augment, for example, as discussed above). In another implementation, the post 40A has one portion that ratchets relative to another to achieve incremental changes in length to support different expanded positions of the expandable augment 100A. In another implementation the post 40A can be slidably coupled to the first plate 10A and second plate 20A so that it moves between a position generally parallel to the first and second plates 10A, 20A (when the expandable augment 100A is in the closed position), different angular positions as the first plate 10A is moved away from the second plate 20A, and/or a position generally perpendicular to one or both of the first and second plates 10A, 20A when the expandable augment 100A is in a maximum expanded position. In another implementation, the post 40A is of a material that plastically deforms when stretched (e.g., allowing the incremental change in length of the post 40A and therefore the incremental change in expanded state of the expandable augment 40A). In one implementation, the post 40A can have a circular cross-section. In another implementation, the post 40A can have a non-circular (e.g., square, rectangular) cross-section. Though FIG. 8A shows one post 40A, one of skill in the art will recognize that the expandable augment 100A can have multiple posts between the first plate 10A and the second plate 20A.

Figure 8B:
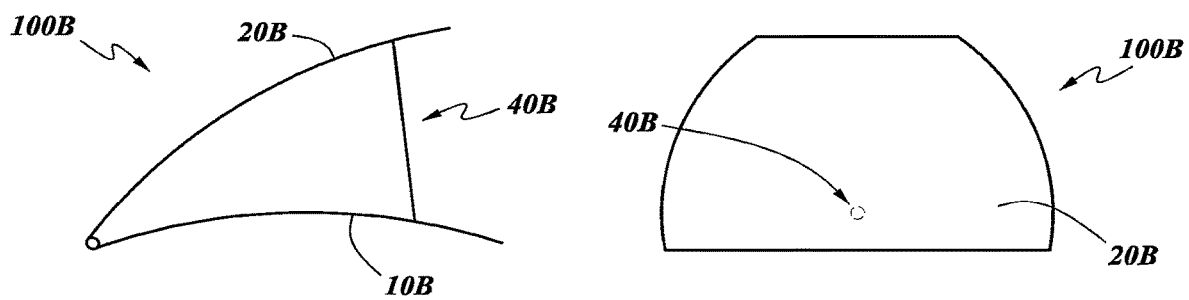
FIG. 8B shows a schematic side view and top view of an expandable augment with a support structure.

FIG. 8B shows a schematic side view (left image) and top view (right image) of an expandable augment module 100B. Some of the features of the expandable augment module 100B are similar to features of the expandable augment module 100A in FIG. 8A, which is based on the expandable augment 100, 100', 100" in FIGS. 1-7B. Thus, reference numerals used to designate the various components of the expandable augment module 100B are identical to those used for identifying the corresponding components of the expandable augment module 100A in FIG. 8A, except that a "B" instead of an "A" has been added to the numerical identifier. Therefore, the structure and description for the various features of the expandable augment module 100A in FIG. 8A, which incorporates the description for the expandable augment 100, 100', 100" in FIGS. 1-7B, are understood to also apply to the corresponding features of the expandable augment module 100B in FIG. 8B, except as described below.

The expandable augment module 100B differs from the expandable augment module 100A in that the support structure 40B is a post (e.g., linear member) 40B that extends between the first plate 10B and the second plate 20B proximate (e.g., near, adjacent) the opening of the expandable augment module 100B. The post 40B can have a similar (e.g., same, identical) structure as the post (e.g., linear member) 40A described above (e.g., have telescoping portions, have ratchet portions, have plastically deformable portion).

Figure 8C:
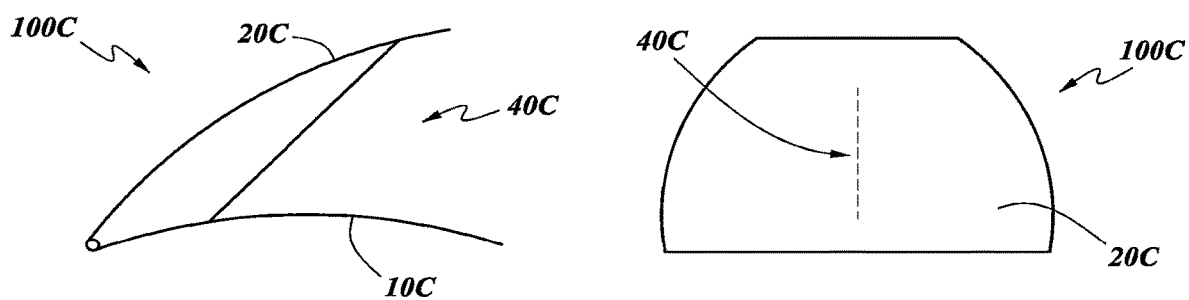
FIG. 8C shows a schematic side view and top view of an expandable augment with a support structure.

FIG. 8C shows a schematic side view (left image) and top view (right image) of an expandable augment module 100C. Some of the features of the expandable augment module 100C are similar to features of the expandable augment modules 100A and 100B in FIGS. 8A-8B, which are based on the expandable augment 100, 100', 100" in FIGS. 1-7B. Thus, reference numerals used to designate the various components of the expandable augment module 100C are identical to those used for identifying the corresponding components of the expandable augment modules 100A and 100B in FIGS. 8A-8B, except that a "C" has been added to the numerical identifier. Therefore, the structure and description for the various features of the expandable augment modules 100A and 100B in FIGS. 8A-8B, which incorporates the description for the expandable augment 100, 100', 100" in FIGS. 1-7B, are understood to also apply to the corresponding features of the expandable augment module 100C in FIG. 8C, except as described below.

The expandable augment module 100C differs from the expandable augment modules 100A and 100B in that the support structure 40C is a post (e.g., linear member) 40C that extends at an angle (e.g., a non-perpendicular angle, an acute angle) relative to the first plate 10C and to the second plate 20C. The post (e.g., linear member) 40C can have a first end attached to the second plate 20C proximate the opening of the expandable augment module 100C and a second end attached to the first plate 10C proximate the closed end (e.g. hinge end) of the expandable augment module 100C. In another implementation, the first end of the post 40C can attached to the first plate 10C proximate the opening of the expandable augment module 100C and a second attached to the second plate 20C proximate the closed end (e.g. hinge end) of the expandable augment module 100C. The post 40C can have a similar (e.g., same, identical) structure as the post (e.g., linear member) 40A described above (e.g., have telescoping portions, have ratchet portions, have plastically deformable portion).

Figure 8D:
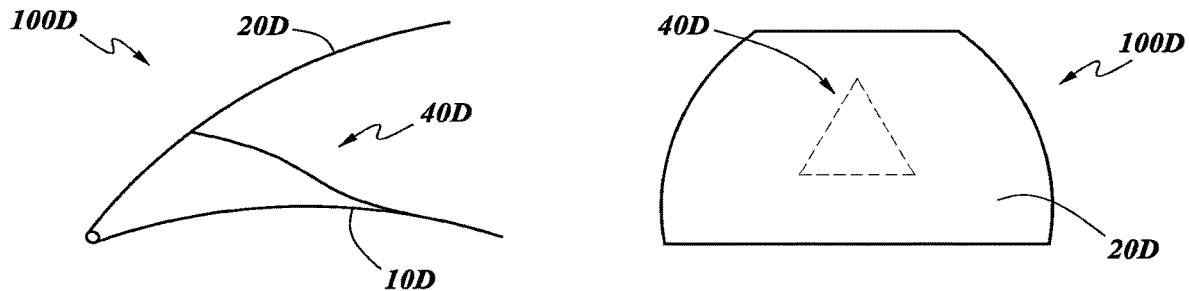
FIG. 8D shows a schematic side view and top view of an expandable augment with a support structure.

FIG. 8D shows a schematic side view (left image) and top view (right image) of an expandable augment module 100D. Some of the features of the expandable augment module 100D are similar to features of the expandable augment module 100C in FIGS. 8C, which is based on the expandable augment 100, 100', 100" in FIGS. 1-7B. Thus, reference numerals used to designate the various components of the expandable augment module 100D are identical to those used for identifying the corresponding components of the expandable augment module 100C in FIG. 8C, except that a "D" has been added to the numerical identifier. Therefore, the structure and description for the various features of the expandable augment module 100C in FIG. 8C, which incorporates the description for the expandable augment 100, 100', 100" in FIGS. 1-7B, are understood to also apply to the corresponding features of the expandable augment module 100D in FIG. 8D, except as described below.

The expandable augment module 100D differs from the expandable augment module 100C in that the support structure 40D is not shaped like a post, but can have an irregular form factor. In the illustrated implementation, the support structure 40D is triangular when viewed from the top (right image) and linear when viewed from the side (left image). However, the support structure 40D can have other shapes (e.g., be rectangular when viewed from the top). The support structure 40D can in one implementation extend at an angle (e.g., a non-perpendicular angle, an acute angle) relative to the first plate 10D and to the second plate 20D. The support structure 40D can have a first end attached to the second plate 20D proximate the closed end (e.g., hinged end) of the expandable augment module 100D and a second end attached to the first plate 10D proximate the open end of the expandable augment module 100D. In another implementation, the first end can be attached to the first plate 10D proximate the closed end (e.g., hinged end) of the expandable augment module 100D and a second end attached to the second plate 10D proximate the open end of the expandable augment module 100. The support structure 40D can have a similar (e.g., same, identical) structure as the support structure 40A described above (e.g., have telescoping portions, have ratchet portions, have plastically deformable portion).

Figure 8E:
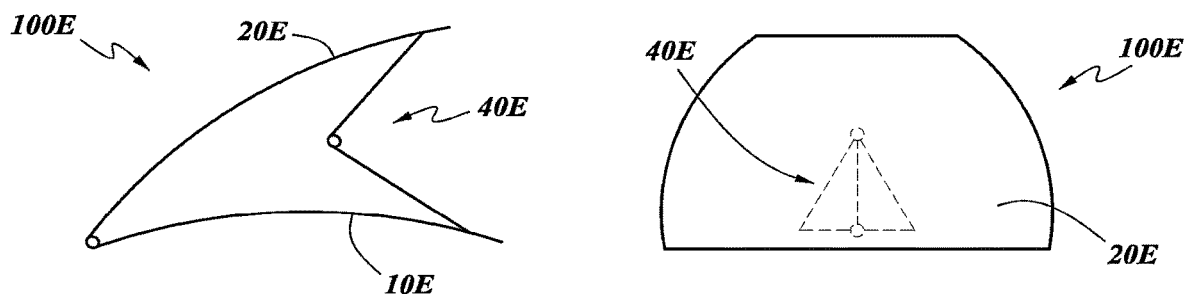
FIG. 8E shows a schematic side view and top view of an expandable augment with a support structure.

FIG. 8E shows a schematic side view (left image) and top view (right image) of an expandable augment module 100E. Some of the features of the expandable augment module 100E are similar to features of the expandable augment module 100D in FIGS. 8D, which is based on the expandable augment 100, 100', 100" in FIGS. 1-7B. Thus, reference numerals used to designate the various components of the expandable augment module 100E are identical to those used for identifying the corresponding components of the expandable augment module 100D in FIG. 8D, except that an "E" has been added to the numerical identifier. Therefore, the structure and description for the various features of the expandable augment module 100D in FIG. 8D, which incorporates the description for the expandable augment 100, 100', 100" in FIGS. 1-7B, are understood to also apply to the corresponding features of the expandable augment module 100E in FIG. 8E, except as described below.

The expandable augment module 100E differs from the expandable augment module 100D in that the support structure has a hinge (e.g. living hinge). In the illustrated implementation, the support structure 40E is triangular (e.g., with the pointed end toward the closed or hinged end of the expandable augment module) when viewed from the top (right image) and has two linear portions connected at a hinged location when viewed from the side (left image). In another implementation, the support structure 40E can be triangular with the pointed end toward the open end of the expandable augment module 100E. However, the support structure 40E can have other shapes (e.g., be rectangular when viewed from the top). The support structure 40E can in one implementation extend at an angle (e.g., a non-perpendicular angle, an acute angle, the same angle) relative to the first plate 10E and to the second plate 20E. The support structure 40E can have a first end attached to the second plate 20E proximate the open end of the expandable augment module 100E and a second end attached to the first plate 10E proximate the open end of the expandable augment module 100E, with the hinged portion disposed further toward the closed end (e.g. hinged end) of the expandable augment module 100E. The hinged portion of the support structure 40E can be a living hinge in one implementation. In another implementation, the hinged portion of the support structure 40E can be a ratcheted hinge, allowing the incremental movement of the support structure 40E to different expanded setpoints to thereby support the incremental opening of the expandable augment module 100E.

Figure 8F:
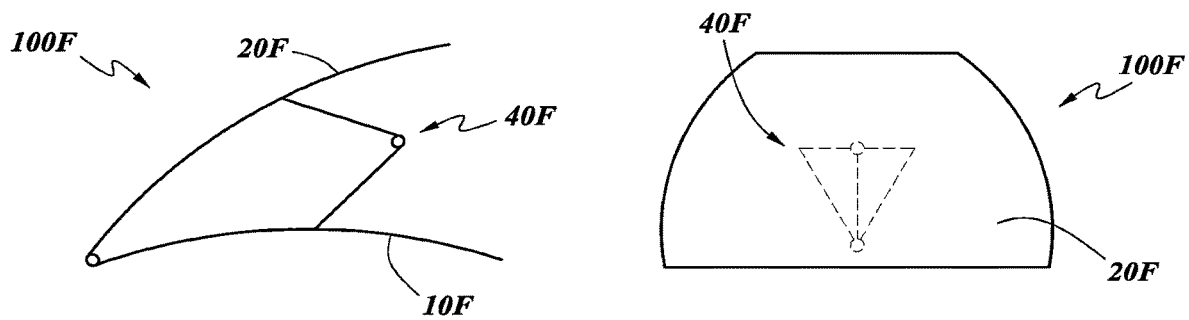
FIG. 8F shows a schematic side view and top view of an expandable augment with a support structure.

FIG. 8F shows a schematic side view (left image) and top view (right image) of an expandable augment module 100F. Some of the features of the expandable augment module 100F are similar to features of the expandable augment module 100E in FIGS. 8E, which is based on the expandable augment 100, 100', 100" in FIGS. 1-7B. Thus, reference numerals used to designate the various components of the expandable augment module 100F are identical to those used for identifying the corresponding components of the expandable augment module 100E in FIG. 8E, except that an "F" has been added to the numerical identifier. Therefore, the structure and description for the various features of the expandable augment module 100ED in FIG. 8E, which incorporates the description for the expandable augment 100, 100', 100" in FIGS. 1-7B, are understood to also apply to the corresponding features of the expandable augment module 100F in FIG. 8F, except as described below.

The expandable augment module 100F differs from the expandable augment module 100E in that it has a support structure 40F with an opposite orientation than that of the support structure 40E.

In the illustrated implementation, the support structure 40F is triangular (e.g., with the pointed end toward the open end of the expandable augment module) when viewed from the top (right image) and has two linear portions connected at a hinged location when viewed from the side (left image). In another implementation, the support structure 40F can be triangular with the pointed end toward the closed or hinged end of the expandable augment module 100F. However, the support structure 40F can have other shapes (e.g., be rectangular when viewed from the top). The support structure 40F can in one implementation extend at an angle (e.g., a non-perpendicular angle, an acute angle, the same angle) relative to the first plate 10F and to the second plate 20F. The support structure 40F can have a first end attached to the second plate 20F proximate the open end of the expandable augment module 100F and a second end attached to the first plate 10F proximate the open end of the expandable augment module 100F, with the hinged portion disposed further toward the open end of the expandable augment module 100F. The hinged portion of the support structure 40F can be a living hinge in one implementation. In another implementation, the hinged portion of the support structure 40F can be a ratcheted hinge, allowing the incremental movement of the support structure 40F to different expanded setpoints to thereby support the incremental opening of the expandable augment module 100F.

Figure 9:
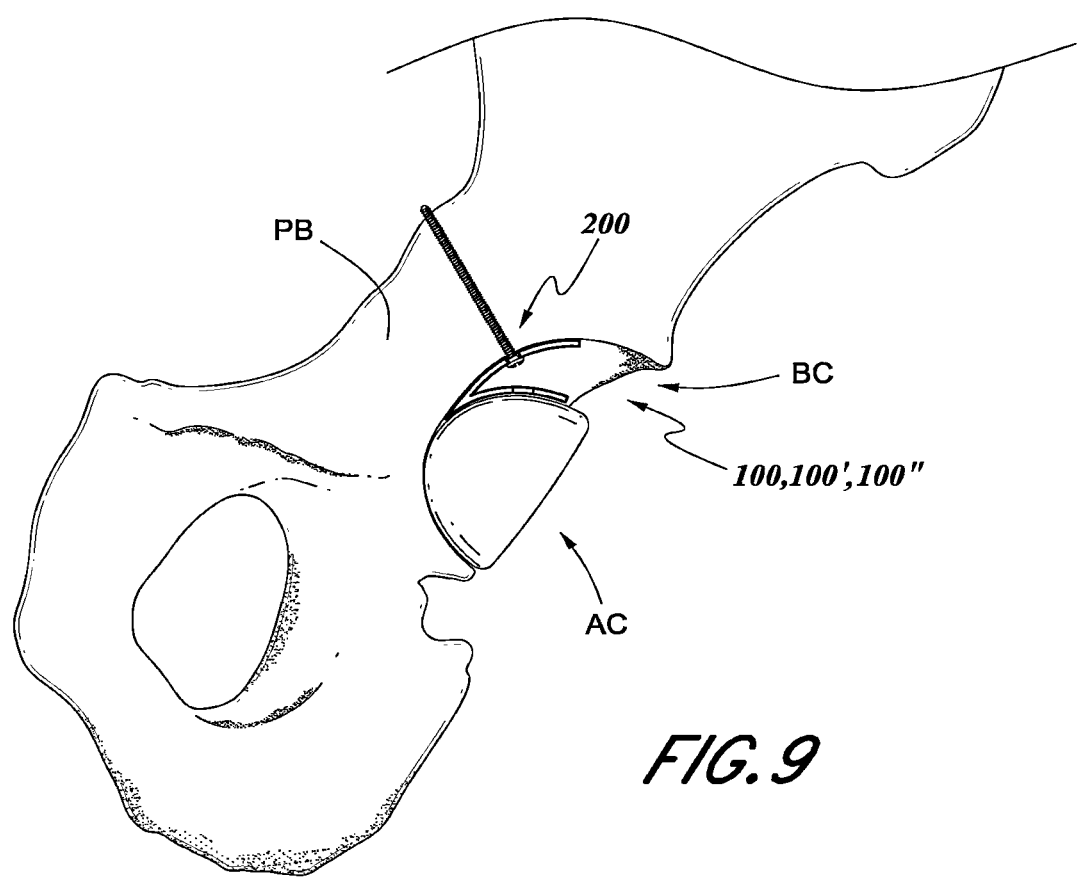
FIG. 9 is a schematic view of an expandable augment implanted in bone and attached to an acetabular cup.

FIG. 9 shows a schematic partial view of an acetabular cup AC implanted in an acetabulum of a pelvis bone PB, where at least a portion of the acetabular cup AC is supported by the expandable augment module 100, 100', 100". The expandable augment module 100, 100', 100" provides structural support to the acetabular cup AC where bone loss or defects in the pelvis bone prevent the implantation of the acetabular cup AC without an augment. Advantageously, the expandable augment module 100, 100', 100" allow the surgeon to evaluate the size of the hole in the acetabulum and evaluate the defects or loss of bone, then attach the expandable augment module 100, 100', 100" to the pelvis bone PB with one or more fasteners 200 (e.g., screws), and adjust (e.g., expand) the expandable augment module 100, 100', 100" (e.g., by moving the first plate 10 away from the second plate 20) to a location where the first plate 10, 10', 10" will support (e.g., contact, engage) an outer surface of the acetabular cup AC. The adjustability of the expandable augment module 100, 100', 100" advantageously allows its use with a variety of different acetabular cup AC sizes, thereby obviating the need for having multiple augment module sizes per acetabular cup size. Once in place, bone cement BC can be applied to fix the acetabular cup to bone, as well as applied between the plates 10, 20 of the expandable augment module 100, 100', 100" to secure the acetabular cup AC and expandable augment module 100, 100', 100" in place. In one implementation, bone cement can be used to fix the acetabular cup AC to the expandable augment module 100, 100', 100". In another implementation, screws can (alternatively or in addition to bone cement) be used to fix the acetabular cup AC to the expandable augment module 100, 100', 100".

Figure 10:
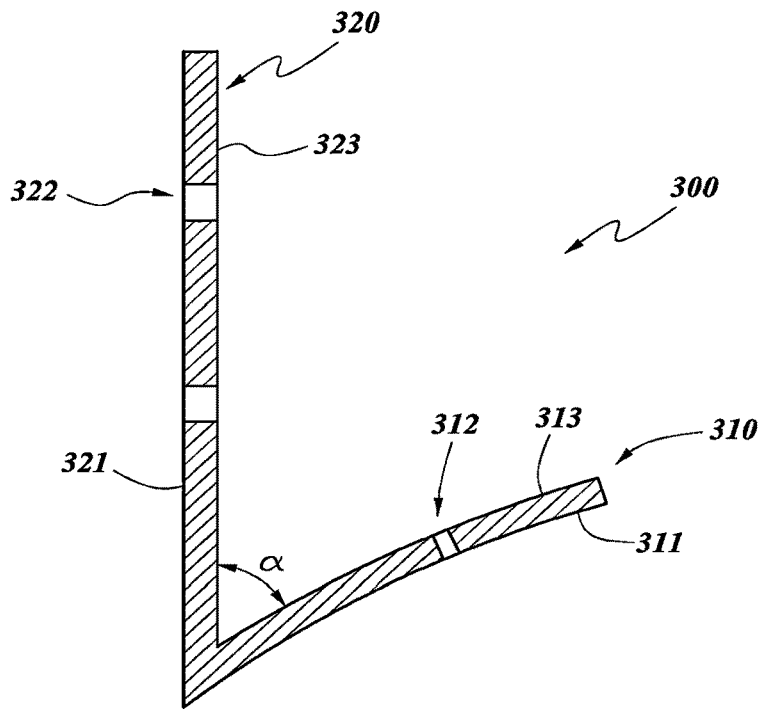
FIG. 10 is a schematic cross-sectional view of a fixed angle augment module.

FIG. 10 shows a cross-sectional view of a fixed angle augment module 300. The fixed angle augment module 300 can have a first plate 310 and a second plate 320 that form a single piece (e.g., monolithic, seamless), where the first plate 310 joins the second plate 320 at a fixed angle α. The fixed angle augment module 300 can optionally be of the same material and have the same profile (e.g., as viewed in top view) as the expandable augment module 100, 100', 100". The first plate 310 can have one or more openings 312 therethrough and the second plate 320 can have one or more openings 322 therethrough. The openings 312, 322 can be aligned so that a fastener 200 can extend through both the openings 312 and the openings 322 at the same time.

Figure 12:
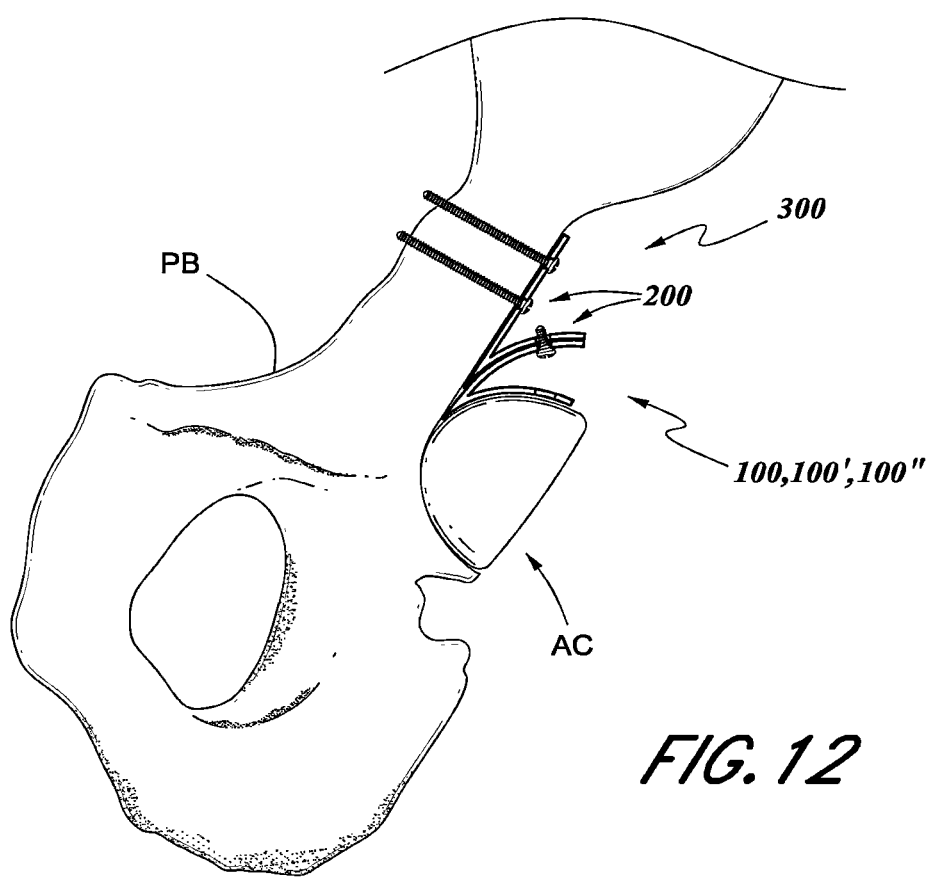
FIG. 12 is a schematic view of the fixed angle augment module attached to bone and the expandable augment, the expandable augment attached to an acetabular cup.

The outer surface 311 of the first plate 310 and the outer surface 321 of the second plate 320 can be porous to facilitate attachment to bone cement and/or bone to aid in solidifying the implantation of the fixed angle augment module 300. For example, where the fixed angle augment module 300 is attached to bone and to the expandable augment module 100 (e.g., as shown in FIG. 12), the porous outer surface 321 of the second plate 320 can facilitate bone in or on growth to aid in solidifying the implantation of the fixed angle augment module 300 to bone. The inner surface 313 of the first plate 310 and the inner surface 323 of the second plate 320 can be porous or rough (e.g., not smooth) to facilitate attachment of bone cement thereto.

Figure 11:
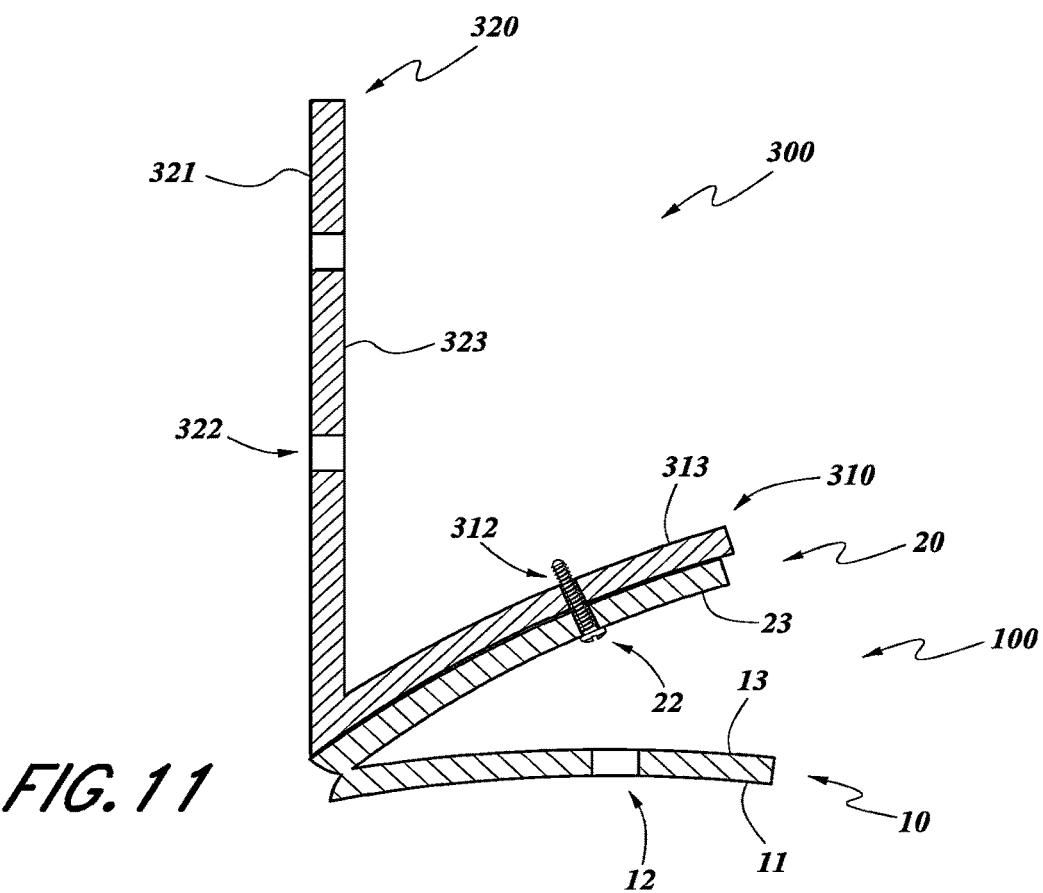
FIG. 11 is a schematic assembled view of a fixed angle augment module and expandable augment.

FIG. 11 shows a cross-sectional view of the fixed angle augment module 300 of FIG. 10 coupled to the expandable augment module 100, 100', 100" with one or more fasteners 200. Though not shown, the fasteners 200 can extend through both the openings 312 and openings 322 of the fixed angle augment module 300 at the same time. Advantageously, the fixed angle augment module 300, when coupled to the expandable augment module 100, 100', 100" allows the support of the acetabular cup AC where the size of the bone loss or defect in the pelvis bone is larger. As shown in FIG. 12, the fixed angle augment module can be fixed to the pelvis bone PB and to the expandable augment module 100, 100', 100". Though FIG. 12 shows separate fasteners 200 coupling the fixed angle augment module 300 to bone PB and separate fasteners 200 coupling the expandable augment module 100, 100', 100" to the fixed angle augment module 300, in some implementations the same fastener couples the expandable augment module 100, 100', 100" to the fixed angle augment module 300, and couples the fixed angle augment module 300 to the pelvis bone PB. The surgeon can then adjust (e.g., expand) the expandable augment module 100, 100', 100" (e.g., by moving the first plate 10 away from the second plate 20) to a location where the first plate 10, 10', 10" will support (e.g., contact, engage) an outer surface of the acetabular cup AC. Once in place, bone cement BC can be applied to fix the acetabular cup to bone, as well as applied between the plates 10, 20 of the expandable augment module 100, 100', 100" and plates 310, 320 of the fixed angle augment module to secure the acetabular cup AC and augment module 100, 100', 100" in place. In one implementation, bone cement can be used to fix the acetabular cup AC to the expandable augment module 100, 100', 100". In another implementation, screws can (alternatively or in addition to bone cement) be used to fix the acetabular cup AC to the expandable augment module 100, 100', 100".

Figure 13:
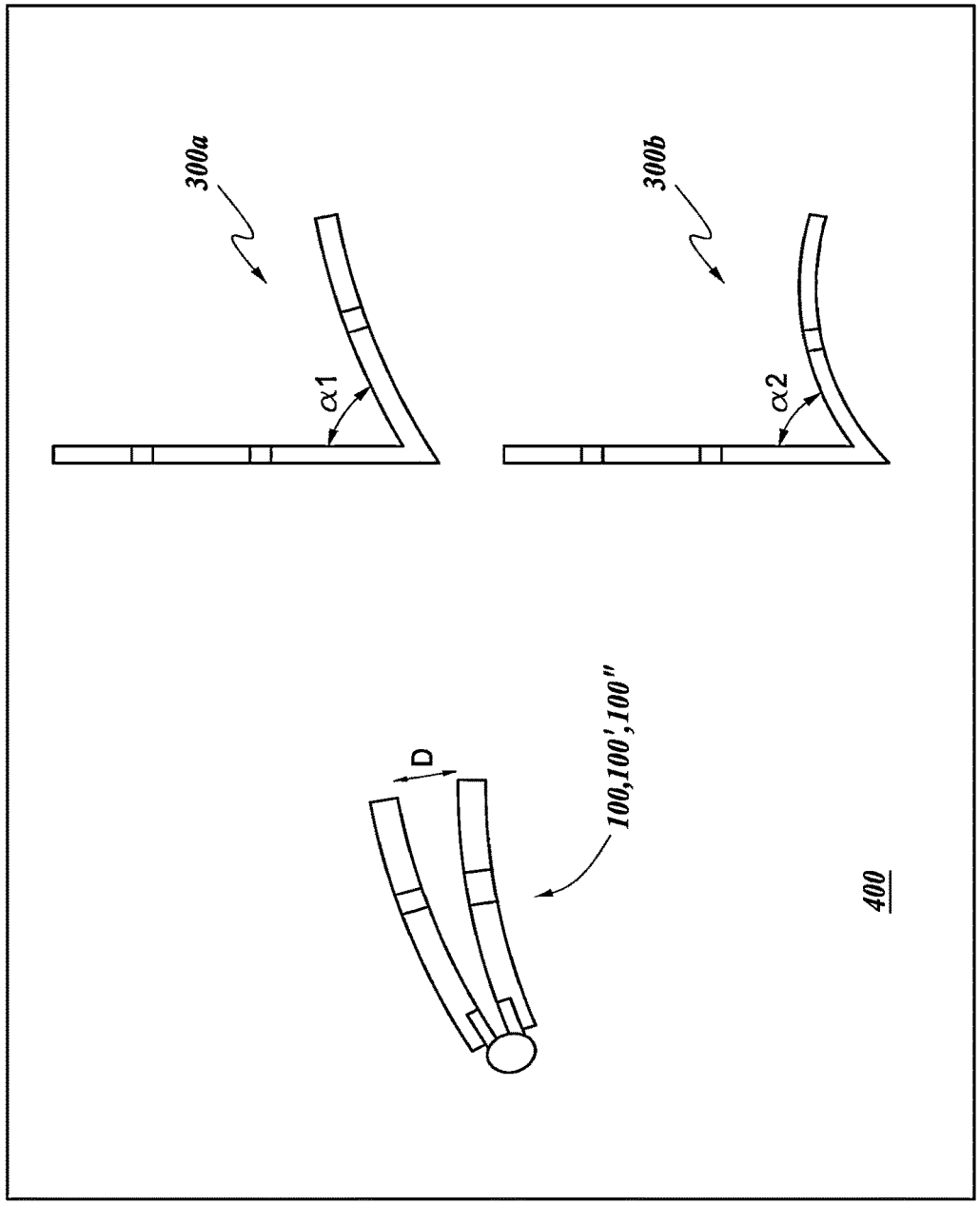
FIG. 13 is a schematic view of a kit including the expandable augment and fixed augment module.

FIG. 13 shows an augment kit 400 for use with an acetabular cup AC in hip joint replacement or revision surgery. The kit 400 can include one or more expandable augment modules 100, 100', 100". The kit 400 can also include multiple fixed angle augment modules, at least two of which can have a different angle between plates of the module. In the illustrated implementation, the kit 400 includes a first fixed angle augment module 300A with first and second plates 310A, 320A joined at a at a fixed angle α1. The kit 400 can also include a second fixed angle augment module 300B with first and second plates 310B, 320B joined at a at a fixed angle α2 smaller than fixed angle α1. The augment kit 400 can be in a single package 410 that includes the expandable augment module 100, 100', 100" and fixed angle augment module(s) 300A, 300B. The augment kit 300 advantageously simplifies the number of augment components needed for use in hip replacement or revision surgery and obviates the need for having multiple augment modules of different sizes for each acetabular cup size.

Figure 14:
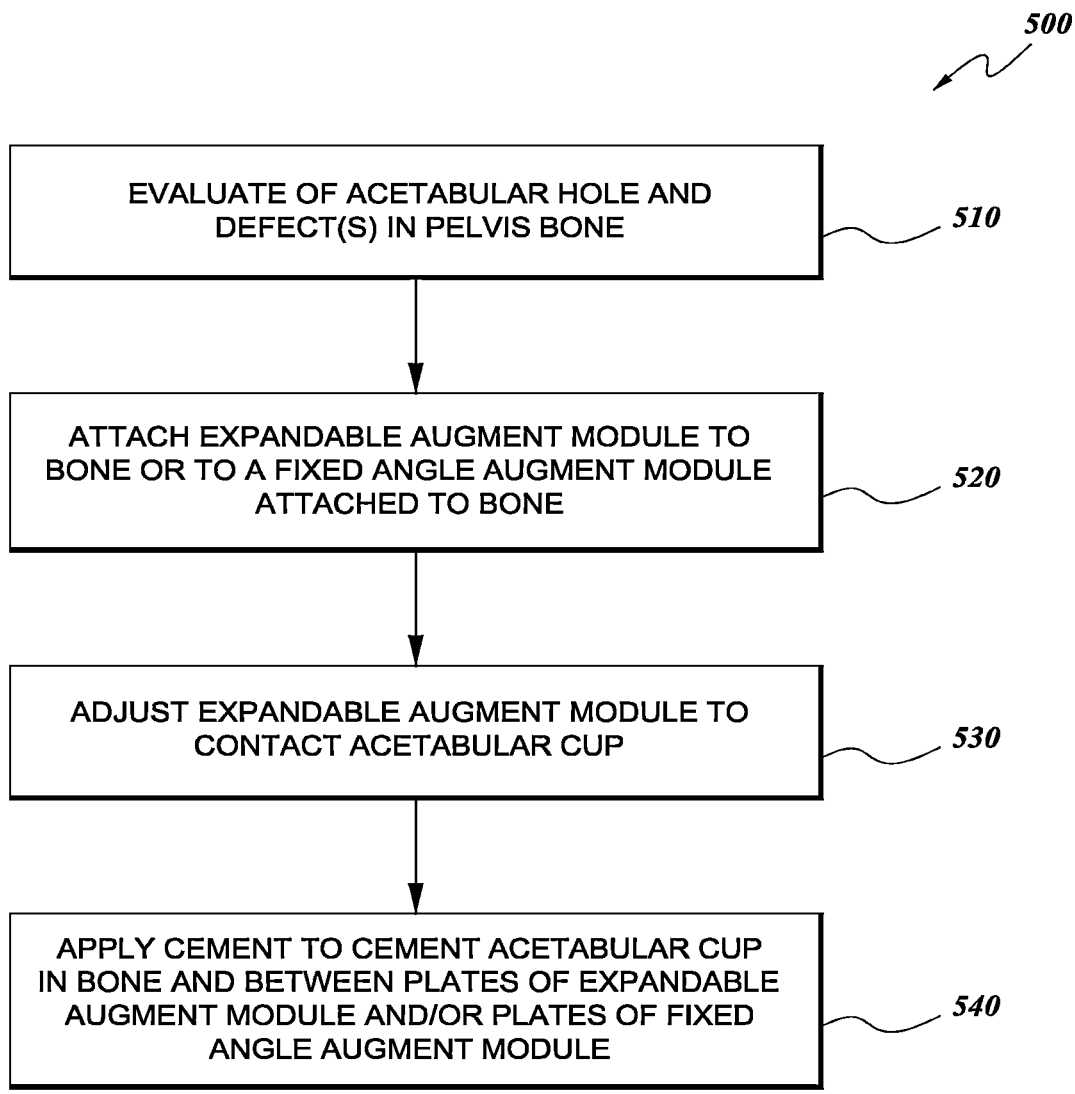
FIG. 14 is a flow chart of a method for using the expandable augment.

FIG. 14 shows a flow chart of a process or method 500 for using an augment in hip joint replacement or revision surgery. The method 500 includes the step 510 of evaluating the size of the acetabular hole in the pelvis bone (e.g., pelvis bone PB in FIGS. 9 and 12). The method 500 also includes the step 520 of attaching an expandable augment module to bone or to a fixed angle augment module that has been attached to bone (as shown in FIGS. 9 and 12). The method 500 also includes the step 530 of adjusting the size of the expandable augment module to support (e.g., contact) the acetabular cup (e.g., as shown in FIGS. 9 and 12). The method 500 also includes the step 540 of applying bone cement to secure the acetabular cup in bone and applying bone cement between plates of the expandable augment module (and between plates of the fixed angle augment module) to secure the acetabular cup assembly in place.

Additional Embodiments

In embodiments of the present disclosure, an augment system for an acetabular cup may be in accordance with any of the following clauses:

Clause 1. An expandable augment module for an acetabular cup, comprising:
a first plate configured to couple with a bone or a fixed augment module, the first plate having one or more first openings configured to receive therethrough corresponding one or more first fasteners, and
a second plate configured to couple to an outer surface of an acetabular cup, the second plate connected to the first plate and configured to pivot relative to the first plate between a first position where the second plate is proximate the first plate along its length and a second position where at least a portion of the second plate is spaced from the first plate, the second plate having one or more second openings configured to be coaxial with the one or more first openings when in the first position, the one or more second openings having a larger size than the one or more first openings.

Clause 2. The expandable augment module of clause 1, wherein the second plate is connected to the first plate by a living hinge.

Clause 3. The expandable augment module of any preceding clause, wherein the second plate is connected to the first plate by a hinge assembly that is separate from the first and second plates.

Clause 4. The expandable augment module of any preceding clause, wherein the second plate has an interface surface that interfaces with the outer surface of the acetabular cup, the interface surface being curved in a widthwise and lengthwise directions.

Clause 5. The expandable augment module of any preceding clause, wherein the first plate has an interface surface that interfaces with the bone or fixed augment module, the interface surface being curved in a widthwise and lengthwise directions.

Clause 6. The expandable augment module of any preceding clause, wherein the first plate has an interface surface that interfaces with the bone or fixed augment module, the interface surface being planar.

Clause 7. The expandable augment module of any preceding clause, wherein the first plate and second plate are interconnected by two or more support members movably coupled to each other and configured to move between a collapsed state in the first position and an expanded state in the second position, the support members configured to support the second plate in the second position and inhibit inadvertent movement of the second plate from said second position.

Clause 8. The expandable augment module of any preceding clause, wherein in the first position the expandable argument body has a thickness of approximately 5 mm.

Clause 9. The expandable augment module of any preceding clause, wherein in the second position the expandable augment body has a thickness of approximately 25 mm.

Clause 10. The expandable augment module of any preceding clause, further comprising the fixed augment module having a third plate and a fourth plate connected to the third plate and extending at a fixed angle relative to the third plate, the third plate having one or more openings configured to receive corresponding fasteners therethrough to couple the fixed augment module to bone, the fourth plate having one or more openings configured to receive the one or more first fasteners therethrough to couple the fixed augment module to the expandable augment body.

Clause 11. An augment kit for an acetabular cup, comprising:
an expandable augment module comprising
a first plate having one or more first openings configured to receive therethrough corresponding one or more first fasteners, and
a second plate configured to couple to an outer surface of an acetabular cup, the second plate connected to the first plate and configured to pivot relative to the first plate between a first position where the second plate is proximate the first plate along its length and a second position where at least a portion of the second plate is spaced from the first plate, the second plate having one or more second openings configured to be coaxial with the one or more first openings when in the first position, the one or more second openings having a larger size than the one or more first openings; and one or more fixed augment modules, each of the fixed augment modules having a third plate, and a fourth plate connected to the third plate and extending at a fixed angle relative to the third plate, the third plate having one or more openings configured to receive corresponding fasteners therethrough to couple the fixed augment module to bone, the fourth plate having one or more openings configured to receive the one or more first fasteners therethrough to couple the fixed augment module to the expandable augment body, wherein at least one of the one or more fixed augment modules has a different fixed angle.

Clause 12. The kit of clause 11, wherein the second plate is connected to the first plate by a living hinge.

Clause 13. The kit of any of clauses 11-12, wherein the second plate is connected to the first plate by a hinge assembly that is separate from the first and second plates.

Clause 14. The kit of any of clauses 11-13, wherein the second plate has an interface surface that interfaces with the outer surface of the acetabular cup, the interface surface being curved in a widthwise and lengthwise directions.

Clause 15. The kit of any of clauses 11-14, wherein the first plate has an interface surface that interfaces with the bone or fixed augment module, the interface surface being curved in a widthwise and lengthwise directions.

Clause 16. The kit of any of clauses 11-15, wherein the first plate has an interface surface that interfaces with the bone or fixed augment module, the interface surface being planar.

Clause 17. The kit of any of clauses 11-16, wherein the first plate and second plate are interconnected by two or more support members movably coupled to each other and configured to move between a collapsed state in the first position and an expanded state in the second position, the support members configured to support the second plate in the second position and inhibit inadvertent movement of the second plate from said second position.

Clause 18. The kit of any of clauses 11-17, wherein in the first position the expandable argument body has a thickness of approximately 5 mm.

Clause 19. The kit of any of clauses 11-18, wherein in the second position the expandable augment body has a thickness of approximately 25 mm.

Clause 20. A method for implanting an acetabular cup, comprising:

evaluating a size of an acetabular hole and one or more defects in a pelvis bone proximate the acetabulum;

attaching an expandable augment module of any preceding clause to the pelvis bone or to a fixed angle augment module attached to the pelvis bone;

adjusting a size of the expandable augment module to contact an acetabular cup; and applying cement between the acetabular cup and bone, and applying cement between plates of the expandable augment module or plates of the fixed angled augment module to thereby fix the acetabular cup in the bone.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. An expandable augment module for an acetabular cup, comprising:
   a first plate extending from a first end to a second end configured to couple with a bone or a fixed augment module, the first plate having a convex first surface and a concave second surface opposite the convex first surface that extend from the first end to the second end; and
   a second plate extending from a third end to a fourth end, the third end attached to the first end via a living hinge so that the second plate is configured to pivot relative to the first plate between a first position where the second plate is proximate the first plate along its length and a second position where at least a portion of the second plate is spaced from the first plate, the second plate having a convex third surface and a concave fourth surface opposite the convex third surface that extend from the third end to the fourth end, the convex third surface configured to face the concave second surface when the expandable augment module is in a collapsed position, the concave fourth surface configured to couple to an outer surface of an acetabular cup.

2. The expandable augment module of claim 1, wherein the first plate comprises one or more first openings configured to receive therethrough corresponding one or more first fasteners, wherein the second plate comprises one or more second openings configured to be coaxial with the one or more first openings when in the first position, the one or more second openings having a larger size than the one or more first openings.

3. The expandable augment module of claim 2, wherein the one or more first openings and the one or more second openings are sized to allow one or more first fasteners to be inserted through the one or more first openings and the one or more second openings in the first position to couple the first plate to a bone or a fixed augment module and allows the second plate to pivot relative to the first plate to the second position.

4. The expandable augment module of claim 2, wherein one of the one or more second openings align with a cutout in an end of the first plate.

5. The expandable augment module of claim 1, wherein the second plate has an interface surface configured to interface with an outer surface of the acetabular cup, the interface surface being curved in a widthwise direction and a lengthwise direction.

6. The expandable augment module of claim 1, wherein the first plate has an interface surface configured to interface with the bone or fixed augment module, the interface surface being curved in a widthwise direction and a lengthwise direction.

7. The expandable augment module of claim 1, wherein in the first position, the expandable augment module has a thickness of approximately 5 mm.

8. The expandable augment module of claim 1, wherein in the second position, the expandable augment module has a thickness of approximately 25 mm.

9. The expandable augment module of claim 1, wherein the second plate is hinged to the first plate.

10. The expandable augment module of claim 1, wherein the second end is wider than the first end.

11. The expandable augment module of claim 1, wherein the fourth end is wider than the third end.

12. The expandable augment module of claim 1, wherein the first plate is one piece with the second plate, and wherein the living hinge is a portion of reduced thickness relative to a thickness of the first plate and a thickness of the second plate.

13. An expandable augment module for an acetabular cup, comprising:
   a first plate extending from a first end to a second end configured to couple with a bone or a fixed augment module, the first plate being curved in a widthwise direction and a lengthwise direction that extends from the first end to the second end; and
   a second plate extending from a third end to a fourth end, the third end attached by a hinge to the first end so that the second plate is attached to the first plate and configured to pivot relative to the first plate between a first position where the second plate is proximate the first plate along its length and a second position where at least a portion of the second plate is spaced from the first plate, the second plate being curved in a widthwise direction and a lengthwise direction that extends from the third end to the fourth end.

14. The expandable augment module of claim 13, further comprising two linear portions extending between the first plate and the second plate, wherein the two linear portions are connected with a hinge.

15. An expandable augment module for an acetabular cup, comprising: a first plate configured to couple with a bone or a fixed augment module, the first plate being curved in a widthwise direction and a lengthwise direction; and a second plate attached to the first plate and configured to pivot relative to the first plate between a first position where the second plate is proximate the first plate along its length and a second position where at least a portion of the second plate is spaced from the first plate, the second plate being curved in a widthwise direction and a lengthwise direction, further comprising two linear portions extending between the first plate and the second plate, wherein the two linear portions are connected with a hinge, wherein the hinge that connects the two linear portions comprises a ratcheted hinge.

16. The expandable augment module of claim 14, wherein the hinge that connects the two linear portions is positioned proximate an open end of the first and second plates.

17. An expandable augment module system for an acetabular cup, comprising:
   an expandable augment module comprising:
   a fixed angle augment module having two plates having a fixed angle therebetween;
   a first plate extending from a first end to a second end, the first plate configured to couple with the fixed angle augment module, the first plate having a convex first surface and a concave second surface opposite the convex first surface that extend from the first end to the second end; and
   a second plate extending from a third end to a fourth end, the third end attached to the first end so that the second plate is configured to pivot relative to the first plate between a first position where the second plate is proximate the first plate along its length and a second position where at least a portion of the second plate is spaced from the first plate forming a second angle, the second plate having a convex third surface and a concave fourth surface opposite the convex third surface that extend from the third end to the fourth end, the convex third surface configured to face the concave second surface when the expandable augment module is in a collapsed position, the concave fourth surface configured to couple to an outer surface of an acetabular cup.

* * * * *